(12) United States Patent
Trofast

(10) Patent No.: US 6,199,607 B1
(45) Date of Patent: *Mar. 13, 2001

(54) FORMULATION FOR INHALATION

(75) Inventor: Jan Trofast, Lund (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/401,592

(22) Filed: Sep. 22, 1999

Related U.S. Application Data

(63) Continuation of application No. 09/005,306, filed on Jan. 9, 1998, now Pat. No. 5,983,956.

(30) Foreign Application Priority Data

Jan. 20, 1997 (SE) ................................. 97-0000134

(51) Int. Cl.[7] ................................. A61K 31/165
(52) U.S. Cl. ................................. 141/392; 141/1; 514/360
(58) Field of Search .................. 141/1, 392; 514/360

(56) References Cited

U.S. PATENT DOCUMENTS

| | | | |
|---|---|---|---|
| 4,161,516 | * 7/1979 | Bell | 424/14 |
| 4,199,578 | 4/1980 | Stevenson | 424/240 |
| 4,414,209 | * 11/1983 | Cook et al. | 424/243 |
| 4,524,769 | 6/1985 | Wetterlin | 128/203.15 |
| 4,534,345 | 8/1985 | Wetterlin | 128/203.15 |
| 4,590,206 | * 5/1986 | Forrester et al. | 514/456 |
| 5,143,126 | * 9/1992 | Boesch et al. | 141/1 |
| 5,192,548 | 3/1993 | Velasquez et al. | 424/443 |
| 5,355,872 | 10/1994 | Riggs et al. | 128/200.21 |
| 5,474,759 | 12/1995 | Fassberg et al. | 424/45 |
| 5,503,869 | 4/1996 | Van Oort | 427/2.14 |
| 5,538,999 | 7/1996 | Clark et al. | 514/653 |
| 5,551,489 | * 9/1996 | Trofast et al. | 141/18 |
| 5,562,923 | 10/1996 | Trofast et al. | 424/489 |
| 5,614,514 | 3/1997 | Axelsson et al. | 514/174 |
| 5,628,307 | 5/1997 | Clark et al. | 128/203.15 |
| 5,637,620 | * 6/1997 | Trofast et al. | 514/630 |
| 5,647,347 | 7/1997 | Van Oort | 128/203.15 |
| 5,654,007 | 8/1997 | Johnson et al. | 424/489 |
| 5,655,523 | 8/1997 | Hodson et al. | 128/315 |
| 5,674,860 | 10/1997 | Carling et al. | 514/171 |
| 5,674,861 | 10/1997 | Andersson et al. | 514/174 |
| 5,700,410 | * 12/1997 | Nakamichi et al. | 264/122 |
| 5,709,884 | 1/1998 | Trofast et al. | 424/489 |
| 5,736,124 | 4/1998 | Akehurst et al. | 424/45 |

FOREIGN PATENT DOCUMENTS

| | | | |
|---|---|---|---|
| WO 93/11773 | 6/1993 | (WO) . | |
| 95/05805 | * 2/1995 | (WO) | 424/489 |
| WO 95/09616 | 4/1995 | (WO) . | |
| WO 98/15280 | 4/1998 | (WO) . | |

OTHER PUBLICATIONS

Dutch Search Report, Jul. 6, 1998 (2 pages).

* cited by examiner

*Primary Examiner*—J. Casimer Jacyna
(74) *Attorney, Agent, or Firm*—Fish & Richardson P.C.

(57) ABSTRACT

A dry powder composition comprising formoterol and a carrier substance, both of which are in finely divided form, wherein the formulation has a poured bulk density of from 0.28 to 0.38 g/ml is useful in the treatment of respiratory disorders.

13 Claims, No Drawings

FORMULATION FOR INHALATION

This application is a continuation of U.S. patent application Ser. No. 09/005,306, filed Jan. 9, 1998, now U.S. Pat. No. 5,983,956.

FIELD OF THE INVENTION

The present invention provides a new pharmaceutical formulation, its preparation and its use.

BACKGROUND TO THE INVENTION

Potent drugs for administration by inhalation are generally formulated in association with carriers such as lactose because of the problem of preparing accurate doses. When such drugs are diluted, variations in the weight of the formulation result in a smaller drug dosage variation rate compared with when they are not diluted. These formulations have generally consisted of coarse particles of the carrier with fine particles of the drug, which combination is generally known as an ordered mixture.

The invention provides an improved formulation which, in systems designed to imitate inhalation has been found to give an improved dispersion of the drug.

DESCRIPTION OF THE INVENTION

According to the invention there is provided a dry powder composition comprising an active substance which is formoterol, a pharmaceutically acceptable salt or solvate thereof, or a solvate of such a salt, and a carrier substance, both of which are in finely divided form, wherein the formulation has a poured bulk density of from 0.28 to 0.38 g/ml, preferably from 0.30 to 0.36 g/ml.

The poured bulk density according to the present invention is measured using known techniques, for example those described in "Powder testing guide: Methods of measuring the physical properties of Bulk powders" L. Svarovsky, Elsevier Applied Science 1987, pp 84–86.

Suitable physiologically acceptable salts of formoterol include acid addition salts derived from inorganic and organic acids, for example the chloride, bromide, sulphate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, gluconate, tricarballylate, hydroxynaphthalene-carboxylate or oleate salts or solvates thereof. The active substance is preferably formoterol fumarate, especially as the dihydrate.

The carrier substance is preferably a mono-, di- or polysaccharide, a sugar alcohol or another polyol. Suitable carriers are, for example, lactose, glucose, raffinose, melezitose, lactitol, maltitol, trehalose, sucrose, mannitol; and starch. Lactose is particularly preferred, especially in the form of its monohydrate.

The ingredients of the formulation according to the invention must both be in a finely divided form, i.e. their mass median diameter should generally be less than 10 $\mu$m, preferably from 1 to 7 $\mu$m, as measured by a laser diffraction instrument or a coulter counter. The ingredients may be produced in the desired particle size using methods known to those of skill in the art, e.g. milling, micronisation or direct precipitation.

The composition according to the invention is preferably formulated to comprise, as a daily dose, from 5 to 250 nmol, more preferably from 15 to 120 nmol of the active substance. When the active substance is formoterol fumarate dihydrate, the composition is preferably formulated to provide a daily dose of from 3 to 96 $\mu$g, more preferably from 3 to 48 $\mu$g and most preferably from 3 to 24 $\mu$g of formoterol fumarate dihydrate. More preferably the composition is formulated to provide unit doses of 3, 4.5, 6, 9 or 12 $\mu$g of formoterol fumarate dihydrate. The composition is preferably formulated to comprise in each unit dose from 50 $\mu$g to 25 mg of the carrier substance, more preferably from 50 $\mu$g to 10 mg, most preferably from 100 to 4000 $\mu$g.

According to the invention there is further provided a process for preparing a composition according to the invention which comprises (a) micronizing the active substance and the carrier substance;

(b) optionally conditioning the product; and (c) spheronizing until the desired bulk density is obtained.

The process preferably further comprises a low energy remicronization step after step (b).

The formulation according to the invention may be made by conventional techniques known per se. Such production processes generally comprise micronizing the ingredients to the required size, removing any amorphous areas on the particles obtained by, for example, the methods described in WO 92/18110 or WO 95/05805 and then agglomerating, spheronizing and sieving the powder obtained. The size of the agglomerates obtained is preferably in the range of from 100 to 2000 $\mu$m, more preferably from 100 to 800 $\mu$m. The bulk density of the formulation produced may be adjusted by varying the components and the process empirically, for example the bulk density can be increased by lengthening the time in which the particles are tumbled in a spheronising device.

In solid-solid mixing, one of the most important features is to ensure content uniformity. The major problem encountered in the powder mixing of fine powders is the inability of mixers to break down powder agglomerates. It has been found that a remicronization step after the conditioning step of the fine powder with low energy input is advantageous. It should generally be carried out using enough energy to break down powder agglomerates but not with so much energy that the size of the particles themselves is affected. Such a step gives a composition wherein the active substance and carrier substance are substantially uniformly distributed, having for example a relative standard deviation of less than 3% (preferably less than 1%) and does not disturb the crystallinity of the fine particles.

The formulation according to the invention may be administered using any known dry powder inhaler, for example the inhaler may be a single or a multi dose inhaler, and may be a breath actuated dry powder inhaler, for example Turbuhaler (trade mark). The invention further provides use of a composition according to the invention in the manufacture of a medicament for use in therapy. The composition according to the invention is useful in the treatment of respiratory disorders, particularly asthma. The invention also provides a method of treating a patient suffering from a respiratory disorder which comprises administering to the patient a therapeutically effective amount of a composition according to the invention.

The invention is illustrated, but not limited, by reference to the following Examples.

EXAMPLE 1

0.0315 Parts of formoterol fumarate dihydrate and 2.969 parts of lactose monohydrate are mixed in a tumbling mixer (Turbula) to an evenly distributed mixture, whereafter the mixture is micronized in a spiral jet mill using a pressure and feeding rate suitable to obtain a particle size of less than 3 μm (mass median diameter as measured by a coulter counter). The micronized particles were then treated using the method disclosed in WO 95/05805 to remove amorphous regions in their crystal structure. The powder was then agglomerated by feeding the powder into a twin screw feeder (K-Tron), sieving in an oscillating sieve (0.5 mm mesh size), spheronizing in a rotating pan with a peripheral speed of 0.5 m/s for 4 minutes and then sieving again using the same sieve, then spheronizing once more for 6 minutes before final sieving (mesh size 1.0 mm) giving a powder with a bulk density of 0.32 g/ml.

EXAMPLE 2

Example 1 was repeated but the powder was remicronized in a spiral jet mill at a lower pressure (about 1 bar) after micronization and conditioning such that the step of treating the particles in the manner described in WO 95/05805 was not required giving a powder with a bulk density of 0.32 g/ml.

What is claimed is:

1. A dry powder composition comprising
   (a) an active substance selected from the group consisting of formoterol, pharmaceutically acceptable salts of formoterol, solvates of formoterol, and solvates of formoterol, and
   (b) a carrier substance selected from the group consisting of monosaccharides, disaccharides, polysaccharides and sugar alcohols,
   wherein both the active substance and the carrier substance are in finely divided form, and the composition has a poured bulk density of from 0.28 to 0.38 g/ml is substantially agglomerated, and is suitable for inhalation.

2. A composition according to claim 1 wherein the active substance is formoterol fumarate dihydrate.

3. A composition according to claim 1 or 2 wherein the bulk density is from 0.30 to 0.36 g/ml.

4. A composition according to claim 1, wherein the active substance and carrier substance are substantially uniformly distributed.

5. A composition according to claim 1 for use in the treatment of a respiratory disorder.

6. A process for preparing a composition according to claim 1 which comprises
   (a) micronizing the active substance and the carrier substance; and
   (b) spheronizing until the desired bulk density is obtained.

7. The process of claim 6 further comprising conditioning the micronized substances.

8. A method of treating a patient suffering from a respiratory disorder which comprises administering to the patient a therapeutically effective amount of a composition according to claim 1.

9. A composition according to claim 1 wherein the carrier substance is selected from the group consisting of lactose, glucose, raffinose, melezitose, lactitol, maltitol, trehalose, sucrose, mannitol and starch.

10. A composition according to claim 1 wherein the carrier substance is lactose monohydrate.

11. A composition according to claim 1 wherein both the active substance and the carrier substance have a mass median diameter of less than 10 μm.

12. A composition according to claim 11 wherein both the active substance and the carrier substance have a mass median diameter of 1 to 7 μm.

13. A dry powder composition comprising
   (a) an active substance selected from the group consisting of formoterol, pharmaceutically acceptable salts of formoterol, solvates of formoterol, and solvates of formoterol salts, and
   (b) a carrier substance,
   wherein both the active substance and the carrier substance have a mass median diameter of less than 10 μm, and the composition has a poured bulk density of from 0.28 to 0.38 g/ml, is substantially agglomerated, and is suitable for inhalation.

* * * * *

UNITED STATES PATENT AND TRADEMARK OFFICE
CERTIFICATE OF CORRECTION

PATENT NO. : 6,199,607 B1
DATED : March 13, 2001
INVENTOR(S) : Jan Trofast

Page 1 of 1

It is certified that error appears in the above-identified patent and that said Letters Patent is hereby corrected as shown below:

<u>Column 1</u>,
Line 34, insert -- , -- after "g/ml"
Line 62, please change "micronisation" to -- micronization --.

Signed and Sealed this

Seventh Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,199,607 B1  
APPLICATION NO. : 09/401592  
DATED : March 13, 2001  
INVENTOR(S) : Jan Trofast Page 1 of 1

It is certified that error appears in the above-identified patent and that said Letters Patent is hereby corrected as shown below:

Title page, Item (30) Foreign Application Priority Data, delete "97-0000134" and insert -- 9700134-1 --.

Signed and Sealed this
Twenty-sixth Day of November, 2013

Margaret A. Focarino
*Commissioner for Patents of the United States Patent and Trademark Office*